United States Patent [19]

Young

[11] 3,987,198

[45] *Oct. 19, 1976

[54] METHOD FOR LOWERING THE FREE FATTY ACID CONTENT IN SEBUM USING CERTAIN FATTY ACID AMIDES

[75] Inventor: John M. Young, Redwood City, Calif.

[73] Assignee: Syntex (U.S.A.) Inc., Palo Alto, Calif.

[ * ] Notice: The portion of the term of this patent subsequent to May 13, 1992, has been disclaimed.

[22] Filed: Jan. 17, 1975

[21] Appl. No.: 541,914

Related U.S. Application Data

[63] Continuation of Ser. No. 406,937, Oct. 16, 1973, Pat. No. 3,883,661, which is a continuation-in-part of Ser. No. 197,117, Nov. 9, 1971, abandoned.

[52] U.S. Cl. ............................................. 424/320
[51] Int. Cl.² ........................................ A61K 27/00
[58] Field of Search ............ 424/320; 252/117, 150

[56] References Cited
UNITED STATES PATENTS

| | | | |
|---|---|---|---|
| 2,089,212 | 8/1937 | Kritchevsky | 260/401 X |
| 2,483,253 | 9/1949 | Young et al. | 252/117 |
| 3,101,300 | 8/1963 | Siegal et al. | 424/71 |
| 3,341,465 | 9/1967 | Kaufman et al. | 252/316 |
| 3,507,806 | 4/1970 | Barker et al. | 252/316 |
| 3,592,930 | 7/1971 | Katz et al. | 424/243 |
| 3,883,661 | 5/1975 | Young | 424/320 |

*Primary Examiner*—Leonard Schenkman
*Attorney, Agent, or Firm*—Joseph I. Hirsch; William B. Walker

[57] ABSTRACT

A method of lowering the free fatty acid content in sebum on the skin surface by topically applying a member of a certain class of fatty acid amides to the affected skin area. Oleic acid diethanolamide is illustrated as a representative of the useful class. After cleansing, rinsing and drying the skin area to be treated, the fatty acid amide formulation is applied thereto and left thereon for beneficial action to occur.

9 Claims, No Drawings

METHOD FOR LOWERING THE FREE FATTY ACID CONTENT IN SEBUM USING CERTAIN FATTY ACID AMIDES

CROSS-REFERENCE TO PARENT APPLICATIONS

This application is a continuation of application Ser. No. 406,937, filed Oct. 16, 1973, now U.S. Pat. No. 3,883,661, which in turn, was a continuation-in-part application of application Ser. No. 197,117, filed Nov. 9, 1971, now abandoned.

The present invention relates to a method for the treatment of acne. More particularly, the present invention is directed to a method for controlling acne by topically applying to the affected skin area a member of a class of certain fatty acid amide compounds, or a pharmaceutically acceptable composition containing a fatty acid amide as the active agent. The present invention also relates to fatty acid amide compositions suitable for use in the aforementioned method.

The disease of acne is well documented. Severe victims may bear the dermatological and psychological scars long after the last lesions have disappeared. The treatment of acne has largely concentrated on the use of "drying" lotions which serve to compromise the effect of the disease, the visual maladies, but not necessarily the cause.

The present invention predisposes the deficiencies of the so-called remedies heretofore employed in the treatment of acne. The present invention prevents the symptoms characteristic of acne from occurring by means of the inhibitory utility of a class of certain fatty acid amide compounds, or compositions having the fatty acid amide as the essential, active component.

The present invention provides a method of treating acne which comprises topically applying to the affected skin area an effective amount of a compound selected from the group consisting of a diethanolamide of a straight or branched chain saturated or unsaturated alkanoic acid containing from 12 to 18 carbon atoms, inclusive, or topically applying to the affected skin area a composition of a pharmaceutically acceptable carrier and, as the essential, active component, a diethanolamide of a straight or branched chain saturated or unsaturated alkanoic acid having 12 to 18 carbon atoms, inclusive.

The present invention, in a second aspect, is directed to a composition consisting essentially of a diethanolamide of an alkanoic acid, as defined above, in admixture with a pharmaceutically acceptable carrier, said composition being suitable for topical application to an acne affected skin area for the purpose of treating and/or controlling the acne condition.

While not intending to be bound by any theoretical explanation of the mechanism of action herein, it is believed that the application of the active compounds defined herein provides control of acne by inhibiting the lipolytic enzymes produced by *Corynebacterium acnes* and other organisms present on the skin surface, which are regarded to be the principal causative agents for the disease of acne or acne vulgaris. It is further postulated that the inhibition of said lipolytic enzymes, as discovered herein, prevents the hydrolytic scission of normal sebum triglycerides which, in turn, precludes the production of long chain fatty acids, the presence of which is believed to cause or induce the inflammation typical of acne lesions. The active compounds hereof are also believed to inhibit the growth of said microorganisms per se. The active compounds defined herein, when employed as topical agents, thus provide an ameliorative effect in the control of acne.

The active compounds of the present invention include:
lauric acid diethanolamide,
myristic acid diethanolamide,
palmitic acid diethanolamide,
oleic acid diethanolamide,
stearic acid diethanolamide,
isostearic acid diethanolamide,
palmitoleic acid diethanolamide,
linoleic acid diethanolamide,
linolenic acid diethanolamide, and
eleostearic acid diethanolamide.

The diethanolamides of oleic, plamitic, lauric, isostearic and myristic acids are the presently preferred active agents. Of these, oleic acid diethanolamide is the agent most preferred at this time.

By the term "effective amount" is meant that amount which serves to effectively control acne with a given individual. This amount can vary over a range depending upon many factors, such as the age of the patient, response to treatment, severity of the condition, and various dermatological and environmental conditions, e.g. sebaceous gland activity, hygiene habits, occupational or drug exposure, and diet. Generally, an effective amount in compositions as herein described will range in concentration from about 0.1% upwards to about 30% or more, by weight, the latter particularly in the initial stages of treatment. Preferably, concentrations of from about 1% to about 10% by weight, are useful.

The term "acne affected skin area" is meant to include that skin area of an individual which has, or is likely to, become affected by acne. This area is characterized by an abundance of sebaceous glands which are most commonly inordinately active in the adolescent years, and include the cheeks and forehead and, to a lesser extent, the neck, back, nape, shoulders and chest. Documented cases of acne affected areas on the entire trunk, legs, and arms exist. In addition, acne cases have been reported from infant years through maturity.

The active compounds of the present invention can be administered alone or they can be conveniently formulated into a suitable composition for topical application to the skin surface. Being generally highly surface active, non-ionic, organic solvent soluble and dispersible in water, they are compatible with a wide variety of topical or cosmetic formulations. Suitable dermatological preparations include ointments, lotions, solutions, tinctures, creams, gels, and aerosols. The particular preparation and its method of formulation is, in general, within the skill of the pharmaceutical arts and is influenced by the diagnosis, effect desired, condition of the patient, inclinations of the physician, and the ability of the pharmacist.

Many formulations known in the art are described, for example, in *American Pharmacy*, Fourth Edition 1955, J. B. Lippincott Co., (particularly Chapters 13, 14, 15, 16, and 17), *Textbook of Pharmaceutical Compounding and Dispensing*, Second Edition, 1955, J. B. Lippincott Co. (particularly Chapter 12), *Remington's Pharmaceutical Sciences*, Fourteenth Edition, 1970, Mark Publishing Co. (particularly Chapter 85), and U.S. Pat. No. 3,592,930 to Katz et al., which publications are hereby incorporated by reference.

Ointments are soft, unctuous, semisolid preparations, usually containing the active agent(s) either in solubilized form or in suspension. A suitable ointment base is one prepared from polyethylene glycol which is liquid at room temperature (eg, one having a molecular weight of about 400).

Lotions are liquid preparations and vary from simple solutions to aqueous or hydroalcoholic preparations containing finely divided substances. The vehicle is made up of suspending or dispersing agents as cellulose derivatives (ethyl cellulose, methyl cellulose, etc.), gelatin and gums, which incorporates the active agent in the vehicle made up of water, alcohol, glycerine, etc.

Solutions are made up of dermatologically acceptable organic solvents where the active ingredient is solubilized. Some of the solvents commonly used are propylene glycol and water.

Tinctures are made up of alcoholic or hydroalcoholic solutions of the active ingredients. Some of the alcohols commonly used in tinctures which are to be used topically are ethanol and isopropanol.

Creams are opaque, soft solids or thick liquids composed of the active ingredient dissolved or suspended in the base. The different cream bases can be classified according to their composition:

a. oil in water type creams which include preparations such as foundation creams, hand creams, shaving creams, etc.,
b. water in oil type creams which include cold creams and emmollient creams, and
c. anhydrous creams (e.g. see U.S. Pat. No. 3,592,930).

Creams are only satisfactory, however, if the components thereof, particularly the oily components thereof, do not adversely affect the effectiveness of the active agent of this invention.

Gels are semi-solid preparations made by gelling a solution or a suspension of the active material in the carrier vehicle. The vehicles, which might be hydrous or anhydrous, are gelled using different gelling agents like carboxy polymethylene (Carbopols by B. F. Goodrich) and neutralized to a proper gel consistency with the use of alkalis like sodium hydroxide and amines like polyoxyethylene-(15)-cocoamine (Ethomeen C/25, Armour Industrial Chemical Company). Presently, gels are the preferred form for application of the active agents of this invention.

Aerosols are made up of solutions or suspensions of active ingredients in an inert carrier which are dispensed with the use of a special spraying device. Some of the carriers commonly used are trichloromonofluoromethane and dichlorodifluoromethane.

The method hereof is usefully practiced as a curative treatment, with daily topical administration being rigorously prescribed or followed as needed. Generally, applications two to four times a day may be necessary, desirable or preferable. Each application of the composition of this invention is left on the skin surface, on the order of hours or so, to permit the percutaneous absorption thereof into the sebaceous glands of the skin, whereby beneficial action in the control of acne occurs.

The active agents of this invention are known nonionic surface active agents which have been incorporated, for detergent or surfactant purposes, into cosmetic, toiletry or pharmaceutical formulations intended to be applied to the surface of the skin (for example, see U.S. Pat. Nos. 3,101,300; 3,101,301; 3,175,949; 3,341,465; and 3,507,806; and Great Britain Pat. Nos. 822,068; 829,426; 1,051,268; 1,103,040; 1,209,560; 1,215,062; 1,233,808; and 1,237,741). Additionally, because of their known surfactant properties, the active agents of this invention are known components of emulsifier or detergent formulations [for example, see U.S. Pat. Nos. 2,089,212 and 2,483,253; and Schwartz & Perry, Surface Active Agents, Vol. 1, 212 (1957)].

The compositions of the present inventions are considered distinct from the compositions described in certain of the aforementioned references because the prior art compositions contain, in addition to the fatty acid diethanolamide surfactant, at least one sebum or sebum-like material or material which would undesirably irritate the skin and/or decrease the effectiveness of the composition if it were used in the treatment of acne (a use which is not taught by such references). By sebum material, it is meant those components which comprise natural sebum on the skin surface, such as free fatty acids, sterol alcohols (such as cholesterol), sterol esters, squalene, wax esters, triglycerides, diglycerides, and monoglycerides, etc. By sebum-like material, it is meant those materials which tend to act like components of natural sebum (and thus may interfere with acne control by adding more of an already overabundant material) or materials which can be converted on the skin surface to sebum materials. The category of sebum-like materials, accordingly, includes mineral oil, spermaceti, fatty oils, lanolin alcohols, waxes, esters or salts of fatty acids, etc. Esters of fatty acids and lower alkanols (eg, isocetyl stearate and isopropyl palmitate), and esters or partial esters of fatty acids and polyhydroxy alcohols or polyhydroxy-containing compounds (eg, hexaglycerol dioleate, polyethylene glycol 400 monooleate, polyglycerol monooleate, and polyglycerol monostearate), are particularly to be avoided since they are hydrolyzed by lipase on the skin surface to give the free fatty acid, the production of which is to be avoided according to the teachings of the present invention.

The active agents of the present invention are the sole active agents in the formulations of this invention (it being understood that a mixture of two or more of the active agents of this invention can be formulated into a composition useful in the treatment of acne, if so desired). This distinguishes the present invention from certain of the above references which incorporate, or utilize, other agents as the active agents of the disclosed preparations in combination with a diethanolamide of a fatty acid utilized for detergent or surfactant purposes.

Since the aforementioned references do not specifically deal with methods or compositions for the treatment of acne, it is apparent that they do not teach or suggest the fundamental aspect of this invention, i.e., that fatty acid diethanolamides (as defined above) can be utilized as active agents in the treatment of acne.

The term "consisting essentially of", as used in this application and appended claims to describe the compositions of this invention, is intended to exclude the presence of sebum, sebum-like, skin irritant, and composition effectiveness-decreasing materials in amounts which interfere with the desired acne-control properties of the compositions, but to permit the presence of other materials in amounts which do not substantially affect said acne-control properties adversely.

The method of the present invention (ie, the manner of topical application of the active agents of this invention) is considered quite distinct from the use of toiletry, cosmetic or detergent formulations which contain various amounts of a diethanolamide of a fatty acid as a surfactant material. A detergent, soap or other cleansing agent is normally applied to the skin to remove, for example, surface dirt, etc. After the washing step is completed, residual detergent, soap or cleansing agent is removed, as by rinsing, to leave the skin surface free of any such materials. The same is true of shampoos with respect to hair and the skin therebeneath. In the present invention, the active agent is applied to a cleaned acne affected skin area, after washing and rinsing, and is permitted to remain thereon to allow percutaneous absorption of the active agent into the sebaceous glands for beneficial action to occur. It is anticipated that the active agent will remain on the acne affected skin area, under a program of continued use, until such time as the treated area is washed and rinsed during the normal course of events. After such washing and rinsing, as with a conventional soap, the active agent of this invention is once again applied to the skin and permitted to remain on the acne affected skin area so as to achieve the beneficial therapeutic effect thereof.

This method of treatment or application of the acne control agents of the present invention is also distinctly different from the use of detergent formulations to treat an acne condition. Routine detergent, or cleansing agent, use in the treatment of acne is generally for the purpose of removing the skin surface lipid film. Thus, the principal purpose is to keep the skin, in the acne affected skin areas, free of oil. Obviously, this is done with wash water and a surfactant, such as a detergent, which assists in removing the oily, hydrophobic materials. However, as indicated above, once the washing operation is completed by the patient, the detergent composition is removed, as by rinsing, from the surface of the skin. Should the detergent happen to contain an amount of an active agent of the present invention, the agent does not, by virtue of the rinsing step, remain on the surface of the skin for a sufficient period of time to have the desired beneficial therapeutic action.

In addition, detergent compositions may contain numerous additional substances which either irritate the skin (eg, excess diethanolamine) and/or decrease the effectiveness of the diethanolamide composition. For example, the monoacid ester or the diacid ester of diethanolamine included in the composition of U.S. Pat. No. 2,483,253 are potential materials for the cleaving of the ester moiety with the concomitant production of, for example, the diethanolamine (an irritant to the skin) and a long chain fatty acid (the production of which is presently considered to be undesirable in the treatment of an acne condition).

Thus, the compositions contemplated by the present invention are intended to be pharmaceutically acceptable formulations containing one or more active agents of this invention in pharmaceutically pure form [ie, excluding sebum or sebum-like materials, and all or substantially all of the materials which irritate the skin (eg, diethanolamine), decrease the effectiveness of the fatty acid diethanolamide, and/or are unnecessary to the appropriate formulation or functioning of a composition intended for use in the treatment of acne]. By "substantially free from" or "excluding substantially all", it is meant that the compositions of this invention include not greater than 5% of impurities which, generally, can not be removed within practical limits. Preferably, the compositions contain less than 3% impurities and, thus, are considered to be pharmaceutically "pure". As set forth above, the composition is intended to be applied to cleaned acne affected skin area and left thereon for beneficial action to occur. This is distinct from the brief application of detergent, shampoo, etc. formulations which are removed shortly after application.

The present invention is also considered distinguishable from the dermatological composition and method of Great Britain Pat. No. 1,051,461. The composition therein described, which contains a fatty amine as the active agent and lauric acid diethanolamide as a nonionic surfactant, is applied to the skin to diminish or inhibit accumulation of lipid materials on the skin surface, and thus is suggested for use in the treatment of acne. The amide is used solely as a non-ionic surfactant; accordingly, there is no suggestion that the fatty acid diethanolamide per se can be used as an active agent in the control of acne. Since the lauric diethanolamide is used as a surfactant, it undoubtedly is obtained from commercial sources and, as such, generally contains at least 25% of impurities (eg, diethanolamine) which would be deleterious to the acne-controlling effectiveness thereof. The present invention is further distinguished from the teachings of the aforementioned patent by the use of the fatty acid diethanolamide as the sole active acne control agent in the compositions of this invention.

The following examples further illustrate the methods by which the present invention can be practiced.

EXAMPLE 1

A 1 ml. aliquot of glyceryl trioleate-(9,10)T is separated on TLC (silica gel) in hexane-ether-acetic acid (70:30:1) and the area corresponding to pure triolein is eluted. The radioactive material is diluted with cold, previously purified triolein (8.8639 g.) in 500 ml. of benzene. The resulting solution is 20mM in triolein.

The crude enzyme prepared by ethanol-acetic acid precipitation from three day cultures of *Corynebacterium acnes* (ATCC No. 6919) is passed successively through Sephadex G-25 and G-100 columns, and the concentrate is diluted to 250 ml. for use in the assay described below.

EXAMPLE 2

An emulsion is prepared by evaporating 5.70 ml. of the benzene solution, prepared in Example 1 above; 6 ml. of 10% gum arabic in water and 3.4 ml. of 0.05M phosphate buffer (pH 7.1) are added, and the mixture is sonicated for three 20 second intervals. Aliquots (0.7 ml.) containing 2 mmoles emulsified triolein are added to each of 10 1/6 dram vials for each compound to be assayed.

Vial No. 1 receives an additional 0.3 ml. buffer at time 0, and acts as 0 control.

Vial Nos. 2–9 receive 0.1 ml. of appropriate dilutions of active compound in water and 0.2 ml. enzyme solution at time 0.

Vial No. 10 receives 0.1 ml. buffer and 0.2 ml. enzyme and acts at 100% control.

The hydrolysis is allowed to proceed for 60 minutes at room temperature, after which time, the vials are transferred to a silicone oil bath and maintained at 95° C. After five minutes, the vials are removed from the bath, and from each a 50 $\mu$l. aliquot is transferred to a 5 × 20 cm. silica gel TLC plate. Each plate is additionally spotted with a mixture of cold standards to facilitate identification and the plates are developed to a height of about 15 cm. in hexane-ether-acetic acid (70:30:1). The areas corresponding to free oleic acid (after visualization with iodine vapor) are scraped directly into scintillation vials and counted.

The counts per minute free oleic acid recovered by TLC from 50 μl. are plotted on semi log paper as Cpm vs. log [active compound], to give a curve from which the concentration producing 50% inhibition is determined for each compound as follows:

| Compound | Concentration Causing 50% Inhibition of Triolein (2mM) Hydrolysis |
| --- | --- |
| Oleic acid diethanolamide | 0.054 mM |
| Palmitic acid diethanolamide | 0.086 mM |
| Lauric acid diethanolamide | 0.11 mM |
| Isostearic acid diethanolamide | 0.14 mM |
| Myristic acid diethanolamide | 0.32 mM |
| 9-Acetamido stearic acid | 0.48 mM |
| N-morpholinooleamide | 0.70 mM |
| Undecylenic diethanolamide | 0.86 mM |
| Undecylenic monoethanolamide | 0.86 mM |
| Oleamide | 4.0 mM |
| Oleic acid | 7.2 mM |
| Diethanolamine | >20.0 mM |

EXAMPLE 3

Culture tubes are prepared containing 10 ml. of freshly prepared Difco Fluid Thioglycollate medium with agar and indicator. For each concentration of each compound, duplicate tubes are prepared by pipetting appropriate aqueous solutions or dispersions into the culture tubes to give final tube concentrations of 50, 25, 12.5, 6.25 and 0 μl/ml. Each tube is inoculated with 0.2 ml. of a 48 hour culture of C. acnes (ATCC No. 6919), and the tubes are inspected at 24 hour intervals. Incubation at 37° C. The results are as follows:

| Compound | Inhibitory Concentration (μg/ml.) at 72 Hours |
| --- | --- |
| Oleic acid diethanolamide | ca. 12.5 |
| Palmitic acid diethanolamide | ca. 6.25 |
| Lauric acid diethanolamide | ca. 12.5 |
| Isostearic acid diethanolamide | ca. 12.5 |
| Myristic acid diethanolamide | ca. 6.25 |
| Undecylenic diethanolamide | >300 |
| Oleic acid | growth stimulatory at 200 μg/ml. |
| Triolein | growth stimulatory at 200 μg/ml. |

The following examples illustrate the manner by which gel, ointment, tincture, and solution formulations can be prepared.

EXAMPLE 4

Oleic acid diethanolamide is dissolved in ethanol with stirring. Carbopol 940 is dispersed in water. The two mixtures are combined with stirring and Ethomeen C-25 is then added to give a gel formulation of the following composition:

| | |
| --- | --- |
| Oleic acid diethanolamide | 30.0% (range 0.01 to 30) |
| Ethanol | 50.0% |
| Carbopol 940 | 1.0% |
| Dist. Water | 18.5% |
| Ethomeen C-25 | 0.5% |
| | 100.0% |

The above procedure is repeated with palmitic acid diethanolamide and propylene glycol in lieu of oleic acid diethanolamide and ethanol.

EXAMPLE 5

Petrolatum is heated to about 60° to 70° C. Oleic acid diethanolamide is added to the melt which is then mixed at room temperature to give an ointment formulation containing from about 0.01 to about 30% oleic acid diethanolamide.

EXAMPLE 6

Oleic acid diethanolamide is dissolved in ethanol to give a tincture formulation containing from about 0.01 to about 30% oleic acid diethanolamide.

EXAMPLE 7

Oleic acid diethanolamide is dissolved in propylene glycol to give a solution formulation containing from about 0.01 to about 30% oleic acid diethanolamide.

EXAMPLE 8

An oleic diethanolamide gel formulation is prepared having the following composition:

| Compound | Weight % |
| --- | --- |
| Oleic acid diethanolamide | 5.0% |
| Ethanol (USP) | 72.0% |
| Carbopol 940 | 1.0% |
| Ethomeen C-25 | 0.5% |
| Dist. Water | 21.5% |
| | 100.0% |

EXAMPLE 9

10 Male and 11 female subjects were treated with the 5% oleic acid diethanolamide of Example 8 in a double-blind crossover study with an initial two-week baseline period, a two-week treatment period, a two-week no-treatment period (or washout period) and a second two-week treatment period. 5 Males and 5 female subjects received the active agent in the first treatment period and a placebo formulation in the second treatment period, while the remaining subjects received the active agent in the second treatment only. The subjects were selected on the basis of having a higher than 20 % free fatty acid content in their individual total sebum. None were on systemic antibiotic therapy during the course of this study.

The subjects were instructed to wash three times daily with Ivory soap, immediately after rinsing and drying the face to apply sufficient medication (active agent or placebo) to cover the entire face with the exception of the eye and cheekbone areas, and to gently massage the medication into the skin. Each treatment was continued for the last 6 weeks of the study, no medication being used, however, during the two-week no-treatment period. No other therapy was permitted on the face during the course of the study. No medicated soaps or shampoos, oily hair dressings or any hair sprays were permitted. Cosmetics other than lipstick and eyeshadow were not to be applied on the days of sebum collection. On days of sebum collection, the forehead was not to be washed, wiped, or touched in the 6 hours between the time of cleansing and the time of sebum collection.

Twice a week during the first two weeks of the study, a forehead sample of surface lipids were obtained from each subject and measured for total weight and free fatty acids. No medication or placebo therapy was employed during this two-week period. These samples from each subject constitute the baseline data for this study. Twice a week for the next 6 weeks, further surface lipid samples were taken from each subject and analyzed. In all cases, the surface lipid samples were collected by drawing sebum from both the left and right sides of the subject's forehead.

A statistical analysis of the results of this study showed that the free fatty acid values determined while the subjects were on oleic acid diethanolamide averaged 11% lower than while the subjects were on placebo. In all instances where the active agent was administered before the placebo, there was an indication of a carryover effect upon the free fatty acid levels, having a duration of at least two weeks and perhaps longer following the termination of its use. The total sebum values while the subjects were on oleic acid diethanolamide averaged 8% lower than while the subjects were on placebo. There is no indication of a carryover effect upon total sebum level, but there is a highly significant trend of decreasing total sebum values over the duration of the study. As set forth earlier in this specification, these reductions in the free fatty acid and total sebum levels are believed to aid in the control of acne by reducing the presence of those skin-surface agents which cause, induce or enhance the disease of acne or acne vulgaris.

Although the treatment period with the active agent during the study was relatively short (ie, two weeks), reductions in free fatty acid levels were effected, as indicated above. Maximum reductions were 78% for one female subject and 66% for one male subject. In addition, comparison of the average values for free fatty acid content in (a) samples obtained immediately prior to treatment with the active medication against (b) the samples obtained at the end of the active medication treatment generally showed an overall reduction of approximately 20%.

It is contemplated that the diethanolamide of the present invention will be used in the treatment of acne for a period of time sufficient to lower free fatty acid and total sebum levels to an appropriate level and to maintain such values at those levels for a desired period of time. It is expected that such usage will be for longer than the two-week period utilized in the study. Thus, in actual use in the treatment of acne, free fatty acid and total sebum value reductions are expected to be greater when therapy is conducted for longer periods of time, with the results of the above study being indicative of the results (ie, reductions) which can be achieved with an active agent of this invention.

One male subject showed slight irritation to the 5% oleic acid diethanolamide utilized. He was shifted to a 1% formulation and, since sensitivity to the active medication subsided, continued on the program.

All data, as presented in this Example, is, of course, subject to change as more studies are conducted with additional test subjects.

While the present invention has been described with reference to specific embodiments thereof, it should be understood by those skilled in this art that various changes may be made and equivalents may be substituted without departing from the true spirit and scope of the invention. In addition, many modifications can be made to adapt a particular situation, material or composition of matter, process, process step or steps, or then-present objective to the spirit of this invention without departing from its essential teachings.

What is claimed is:

1. A method for lowering the free fatty acid content in sebum on the skin surface comprising topically applying to the skin surface an effective amount of a composition consisting essentially of a pharmaceutically acceptable carrier and about 0.1% to about 30% of at least one diethanolamide of a saturated or unsaturated alkanoic acid containing from 12 to 18 carbon atoms, inclusive, and permitting said composition to remain on the skin surface to effect a lowering of the free fatty acid content in the sebum.

2. The method of claim 1 wherein said diethanolamide is oleic acid diethanolamide.

3. The method of claim 1 wherein said diethanolamide is lauric acid diethanolamide.

4. The method of claim 1 wherein said diethanolamide is palmitic acid diethanolamide.

5. The method of claim 1 wherein said composition contains about 1 to about 10% diethanolamide.

6. A method for lowering the free fatty acid content in sebum comprising (a) thoroughly washing a skin area with water and a cleansing agent, (b) rinsing said washed skin area to substantially remove any residual cleansing agent, (c) drying said washed skin area, (d) topically applying to said skin area an effective amount of a composition consisting essentially of a pharmaceutically acceptable carrier and about 0.1% to about 30% of a diethanolamide of a saturated or unsaturated alkanoic acid containing from 12 to 18 carbon atoms, inclusive, and (e) permitting said diethanolamide-containing composition to remain on said skin area to effect a lowering of the free fatty acid content in the sebum.

7. The method of claim 6 wherein said diethanolamide is palmitic acid diethanolamide.

8. The method of claim 6 wherein said diethanolamide is oleic acid diethanolamide.

9. The method of claim 6 wherein the amount of said diethanolamide in said composition is from about 1% to about 10% by weight.

* * * * *